US009409946B2

(12) United States Patent
Callens et al.

(10) Patent No.: US 9,409,946 B2
(45) Date of Patent: *Aug. 9, 2016

(54) PEPTIDE MANUFACTURING PROCESS

(75) Inventors: Roland Callens, Grimbergen (BE);
Laurent Jeannin, Brussels (BE);
Georges Blondeel, Aalst (BE)

(73) Assignee: PEPTISYNTHA, Brussels (BE)

( * ) Notice: Subject to any disclaimer, the term of this patent is extended or adjusted under 35 U.S.C. 154(b) by 10 days.

This patent is subject to a terminal disclaimer.

(21) Appl. No.: 12/999,606

(22) PCT Filed: Jun. 17, 2008

(86) PCT No.: PCT/EP2008/057637
§ 371 (c)(1),
(2), (4) Date: Dec. 16, 2010

(87) PCT Pub. No.: WO2009/152850
PCT Pub. Date: Dec. 23, 2009

(65) Prior Publication Data
US 2011/0092671 A1    Apr. 21, 2011

(51) Int. Cl.
| | |
|---|---|
| *C07K 7/08* | (2006.01) |
| *C07K 5/10* | (2006.01) |
| *C07K 7/06* | (2006.01) |
| *C07K 5/08* | (2006.01) |
| *C07K 5/09* | (2006.01) |
| *C07K 5/097* | (2006.01) |
| *C07K 14/47* | (2006.01) |

(52) U.S. Cl.
CPC ............ *C07K 5/0817* (2013.01); *C07K 5/0821* (2013.01); *C07K 14/4723* (2013.01)

(58) Field of Classification Search
None
See application file for complete search history.

(56) References Cited

U.S. PATENT DOCUMENTS

| | | |
|---|---|---|
| 4,923,966 A | 5/1990 | Callens et al. |
| 4,954,616 A | 9/1990 | Callens et al. |
| 5,262,567 A | 11/1993 | Callens et al. |

FOREIGN PATENT DOCUMENTS

| | | | |
|---|---|---|---|
| WO | WO 9965506 A2 | 12/1999 | |
| WO | WO 2006008050 A1 | * 1/2006 | |
| WO | WO 2008040536 A1 | * 4/2008 | |
| WO | WO 2009153294 A1 | 6/2009 | |

OTHER PUBLICATIONS

Kamysz et al (Polish Journal of Microbiology 2006, vol. 55, No. 4, 303-307).*
Carpino et al (Organic Process Research & Development 2003, 7, 28-37).*
U.S. Appl. No. 12/999,033, filed Dec. 14, 2010, Roland Callens, et al.
Fritsche, Thomas R., et al—"Antimicrobial Activity of Omiganan Pentahydrochloride against Contemporary Fungal Pathogens Responsible for Catheter-Associated Infections", Antimicrobial Agents and Chemotherapy Mar. 2008, vol. 52(3), 1187-1189; 3 pgs.
Kamysz, Wojciech, et al—"In Vitro Activity of Synthetic Antimicrobial Peptides against Candida"—Polish Journal of Microbiology 2006, vol. 55 (4), 303-307; 5 pgs.
Third Office Action in Chinese Patent Application 200980131972.1 dated May 19, 2014 (5 pages).
English Translation of the Third Office Action in Chinese Patent Application 200980131972.1 dated May 19, 2014 (7 pages).
Gran L.; "Isolation of Oxytocic Peptides from Oldenlandia Affinis by Solvent Extraction of Tetraphenylborate Complexes and Chromatography on Sephadex LH-20;" Lloydia.; 1973; 36(2); pp. 207-208.
Office Action in U.S. Appl. No. 12/999,033 mailed on Apr. 7, 2014.
Communication pursuant to Article 94(3) EPC in EP Application No. 08 761 122.4 mailed on Nov. 13, 2014 (4 pages).
Exhibit [A] to the Declaration of Roland Callens dated Sep. 19, 2015; Saul B. Needleman; "Protein Sequence Determination: A Sourcebook of Methods and Techniques;" pp. 276-78 (2013).
Exhibit [B] to the Declaration of Roland Callens dated Sep. 19, 2015; Joullié et al.; "Evolution of Amide Bond Formation;" ARKIVOC; vol. 8, 189-250 (2010).
Exhibit [C] to the Declaration of Roland Callens dated Sep. 19, 2015; Shawn Doonan; "Peptides and Proteins;" Royal Society of Chemistry; pp. 37-38 (2002).
Exhibit [D] to the Declaration of Roland Callens dated Sep. 19, 2015; Van Vranken et al.; "Introduction to Bioorganic Chemistry and Chemical Biology"; pp. 190-191 (2013).

* cited by examiner

*Primary Examiner* — Brian J Gangle
*Assistant Examiner* — Andrea McCollum
(74) *Attorney, Agent, or Firm* — Mayer Brown LLP

(57) ABSTRACT

A process for the manufacture of peptide Omiganan in solution phase. Novel intermediates in the process for the manufacture of Omiganan and processes for the manufacture of these intermediates.

18 Claims, 1 Drawing Sheet

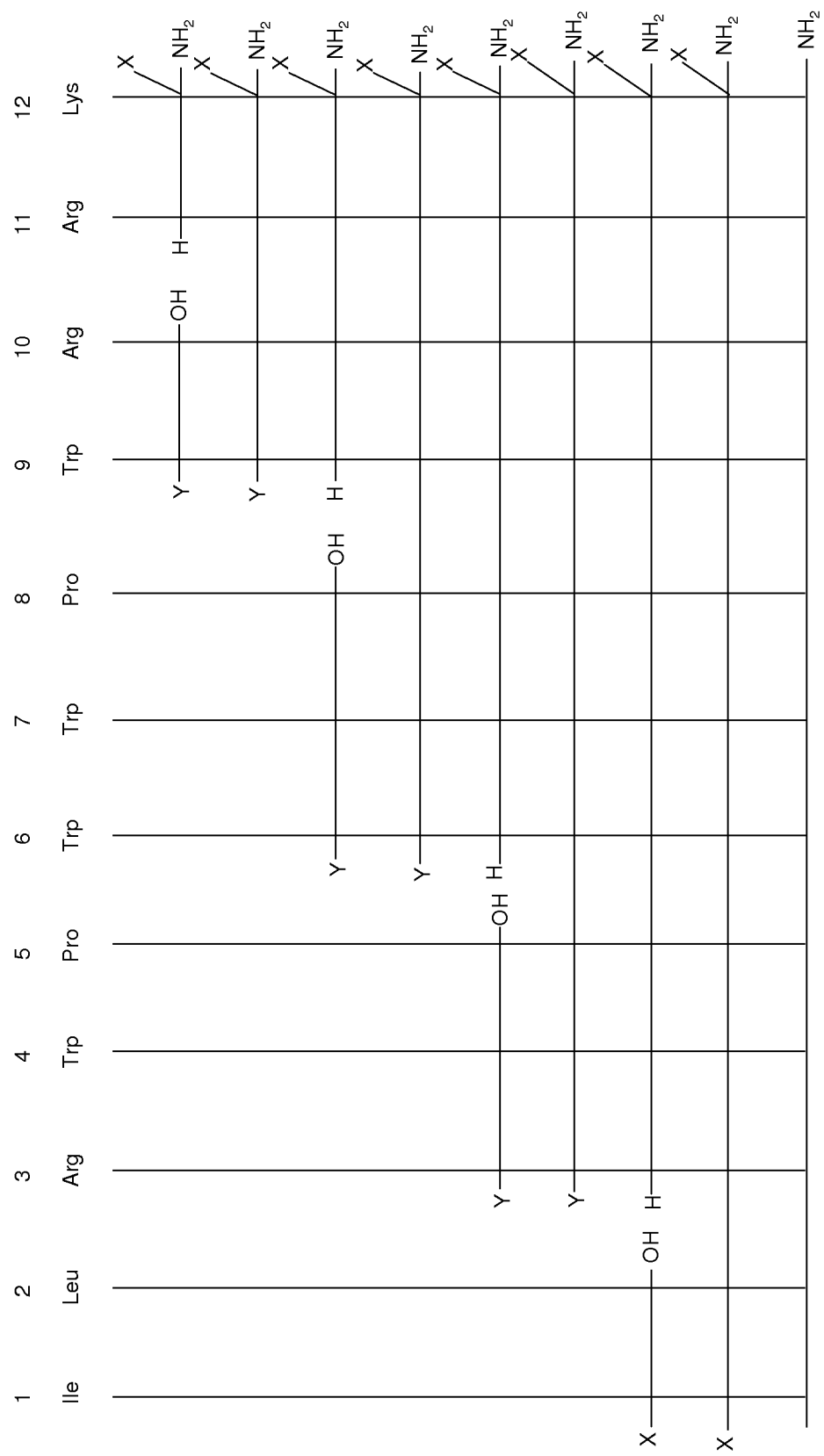

SEQUENCE LISTING

<160> NUMBER OF SEQ ID NOS: 18

<210> SEQ ID NO 1
<211> LENGTH: 12
<212> TYPE: PRT
<213> ORGANISM: Artificial
<220> FEATURE:
<223> OTHER INFORMATION: synthetic peptide

<400> SEQUENCE: 1

```
Ile Leu Arg Trp Pro Trp Trp Pro Trp Arg Arg Lys
1               5                   10

<210> SEQ ID NO 2
<211> LENGTH: 10
<212> TYPE: PRT
<213> ORGANISM: Artificial
<220> FEATURE:
<223> OTHER INFORMATION: synthetic peptide

<400> SEQUENCE: 2

Arg Trp Pro Trp Trp Pro Trp Arg Arg Lys
1               5                   10

<210> SEQ ID NO 3
<211> LENGTH: 7
<212> TYPE: PRT
<213> ORGANISM: Artificial
<220> FEATURE:
<223> OTHER INFORMATION: synthetic peptide

<400> SEQUENCE: 3

Trp Trp Pro Trp Arg Arg Lys
1               5

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Trp Arg Arg Lys
1

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Pro Trp Arg Arg Lys
1               5

<210> SEQ ID NO 6
<211> LENGTH: 6
<212> TYPE: PRT
<213> ORGANISM: Artificial
<220> FEATURE:
<223> OTHER INFORMATION: synthetic peptide

<400> SEQUENCE: 6

Trp Pro Trp Arg Arg Lys
1               5

<210> SEQ ID NO 7
<211> LENGTH: 7
<212> TYPE: PRT
<213> ORGANISM: Artificial
<220> FEATURE:
<223> OTHER INFORMATION: synthetic peptide

<400> SEQUENCE: 7
```

```
Trp Trp Pro Trp Arg Arg Lys
1               5

<210> SEQ ID NO 8
<211> LENGTH: 8
<212> TYPE: PRT
<213> ORGANISM: Artificial
<220> FEATURE:
<223> OTHER INFORMATION: synthetic peptide

<400> SEQUENCE: 8

Pro Trp Trp Pro Trp Arg Arg Lys
1               5

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Trp Pro Trp Trp Pro Trp Arg Arg Lys
1               5

<210> SEQ ID NO 10
<211> LENGTH: 10
<212> TYPE: PRT
<213> ORGANISM: Artificial
<220> FEATURE:
<223> OTHER INFORMATION: synthetic peptide

<400> SEQUENCE: 10

Arg Trp Pro Trp Trp Pro Trp Arg Arg Lys
1               5                   10

<210> SEQ ID NO 11
<211> LENGTH: 11
<212> TYPE: PRT
<213> ORGANISM: Artificial
<220> FEATURE:
<223> OTHER INFORMATION: synthetic peptide

<400> SEQUENCE: 11

Leu Arg Trp Pro Trp Trp Pro Trp Arg Arg Lys
1               5                   10

<210> SEQ ID NO 12
<211> LENGTH: 4
<212> TYPE: PRT
<213> ORGANISM: Artificial
<220> FEATURE:
<223> OTHER INFORMATION: synthetic peptide

<400> SEQUENCE: 12

Trp Pro Trp Arg
1

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Trp Trp Pro Trp Arg
```

```
<210> SEQ ID NO 14
<211> LENGTH: 6
<212> TYPE: PRT
<213> ORGANISM: Artificial
<220> FEATURE:
<223> OTHER INFORMATION: synthetic peptide

<400> SEQUENCE: 14

Pro Trp Trp Pro Trp Arg
1               5

<210> SEQ ID NO 15
<211> LENGTH: 7
<212> TYPE: PRT
<213> ORGANISM: Artificial
<220> FEATURE:
<223> OTHER INFORMATION: synthetic peptide

<400> SEQUENCE: 15

Trp Pro Trp Trp Pro Trp Arg
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16

Arg Trp Pro Trp Trp Pro Trp Arg
1               5

<210> SEQ ID NO 17
<211> LENGTH: 9
<212> TYPE: PRT
<213> ORGANISM: Artificial
<220> FEATURE:
<223> OTHER INFORMATION: synthetic peptide

<400> SEQUENCE: 17

Leu Arg Trp Pro Trp Trp Pro Trp Arg
1               5

<210> SEQ ID NO 18
<211> LENGTH: 10
<212> TYPE: PRT
<213> ORGANISM: Artificial
<220> FEATURE:
<223> OTHER INFORMATION: synthetic peptide

<400> SEQUENCE: 18

Ile Leu Arg Trp Pro Trp Trp Pro Trp Arg
1               5                   10
```

US 9,409,946 B2

PEPTIDE MANUFACTURING PROCESS

CROSS-REFERENCE TO RELATED APPLICATIONS

The present patent application is a U.S. national stage application under 35 U.S.C. §371 of International Application No. PCT/EP2008/057637 filed Jun. 17, 2008, the content of this application being incorporated herein by reference for all purposes.

TECHNICAL FIELD OF THE INVENTION

The invention relates to a process for the manufacture of the peptide Omiganan and its intermediates, and furthermore to novel intermediates in the process for the manufacture of Omiganan.

BACKGROUND OF THE INVENTION

Omiganan is the Common International Denomination (CID) for the peptide H-Ile-Leu-Arg-Trp-Pro-Trp-Trp-Pro-Trp-Arg-Arg-Lys-NH$_2$ (SEQ ID NO 1) that is mostly used in the form of its pentahydrochloride (5 HCl) salt. Omiganan is a cationic antimicrobial peptide. Recent research has also shown that it may play a role in the inflammatory response. Omiganan, in in vitro assay, demonstrated a rapid bactericidal activity against micro-organisms that colonize the skin and that may play a role in the pathogenesis of inflammatory lesions. Omiganan pentachloride is moreover currently in a Phase II-III for treatment of severe acne and in a Phase III clinical trial for the prevention of central venous catheter-related bloodstream infections.

Omiganan can be produced via a linear peptide synthesis wherein the respective amino acids are consecutively added to a growing peptide chain. These processes are unsatisfactory as to yield and purity of the desired peptide Omiganan.

The present invention now makes available an improved synthesis for the peptide Omiganan.

U.S. Pat. No. 5,262,567 discloses the use of a compound including a guanidine group and an unsubstituted tetraphenylborate ion as intermediate in the synthesis of peptides. As an example, the synthesis of the compound formed by arginine and tetraphenylborate (TPB) and its use in the synthesis of the peptide Boc-Leu-Arg-OH is described.

WO 99/65506 A discloses pharmaceutical compositions containing cationic peptides including the cationic peptide MBI 11B20CN which contains the amino acid sequence of Omiganan.

SUMMARY OF THE INVENTION

An object of the present invention is therefore the provision of a process for the production of the peptide Omiganan, which gives Omiganan in high yield and high purity. The process according to the invention allows surprisingly the production of said peptide with a limited number of steps, in particular purification steps, thus greatly reducing manufacturing costs.

The invention thus relates in a first aspect to a process for the manufacture of the peptide Omiganan with the sequence H-Ile-Leu-Arg-Trp-Pro-Trp-Trp-Pro-Trp-Arg-Arg-Lys-NH$_2$ (SEQ ID NO 1) or a derivative thereof comprising at least one step of coupling in solution a first peptide having an activated carboxy group and at least two amino acid units, or an amino acid, selected from the group consisting of Ile, Leu, Arg and Trp, Pro having an activated carboxy group with a second peptide having a free amino group and at least two amino acid units, wherein the first and second peptides are different and contain amino acids selected from the group consisting of Ile, Leu, Arg, Trp, Pro and Lys in the order as prescribed by the sequence Ile-Leu-Arg-Trp-Pro-Trp-Trp-Pro-Trp-Arg-Arg-Lys (SEQ ID NO 1) in Omiganan.

BRIEF DESCRIPTION OF THE DRAWING

For a detailed description of the preferred embodiments of the invention, reference will now be made to the accompanying drawing in which:

FIG. 1 illustrates a scheme of particularly preferred processes according to the invention, in which X and Y may be the same or different.

DETAILED DESCRIPTION OF THE PREFERRED EMBODIMENTS

For the purpose of the present invention, the term "peptide" refers to a polymer in which the monomers are amino acids covalently attached together through amide bonds. Peptides are two or often more amino acids monomers long. In addition, all peptide sequences are represented by formulae whose left to right orientation is in the conventional direction of amino-terminus to carboxy-terminus.

For the purpose of the present invention, the term "amino acid" is intended to denote any compound comprising at least one NR$_1$R$_2$ group, preferably NH$_2$ group, and at least one carboxyl group. The amino acids of this invention can be naturally occurring or synthetic. The natural amino acids, with exception of glycine, contain a chiral carbon atom. Unless otherwise specifically indicated, the compounds containing natural amino acids with the L-configuration are preferred. Amino acids residues are abbreviated as follows throughout the application: Isoleucine is Ile; Leucine is Leu; Arginine is Arg; Tryptophan is Trp; Proline is Pro and Lysine is Lys.

For the purpose of the present invention, the term "C-terminal" of a peptide is the end of an amino acid sequence terminated by a free carboxyl group (—COOH). On the other hand, the term "N-terminal" of a peptide refers to the end of an amino acid sequence terminated by an amino acid with a free amino group (—NH$_2$).

For the purpose of the present invention, the term "coupling" refers to the reaction between the carboxyl group of an amino acid or the C-terminus of a first peptide to the amino group of another amino acid or the N-terminus of a second peptide. In other words, during coupling, two peptide intermediate fragments, or a peptide intermediate fragment and a reactive amino acid, are coupled, generally, in an appropriate solvent, and usually in the presence of additional reagents that promote the efficiency and quality of the coupling reaction. The peptide intermediate fragments are reactively arranged so the N-terminus of one fragment becomes coupled to the C-terminus of the other fragment, or vice versa.

As used herein, the term "peptide derivative" includes an analog in which one or more amino acid residues have been replaced by the corresponding D-isomer or by a non-natural amino acid residue, or a chemical derivative thereof. A chemical derivative of a peptide includes, but is not limited to, a derivative containing additional chemical moieties not normally a part of the peptide provided that the derivative retains the inhibitory activity of the peptide. Examples of such derivatives are: (a) N-acyl derivatives of the amino terminal or of another free amino group, wherein the acyl group may be either an alkanoyl group such as acetyl, hexanoyl, octanoyl;

an aroyl group, e.g., benzoyl, or biotinyl; (b) esters of the carboxyl terminal or of another free carboxyl or hydroxy groups; and (c) amides of the carboxyl terminal or of another free carboxyl groups produced by reaction with ammonia or with a suitable amine. Derivatives of Omiganan and intermediates thereof are also for example protected fragments and peptide of the Omiganan sequence, the salts of Omiganan and intermediates thereof with inorganic or organic acids, preferably inorganic acids and most preferably hydrochloric acid. Examples of salts with organic acids which might be used are the salts with acetic acid, citric acid, oxalic acid, trifluoroacetic acid, tetraphenyl boric acid and tartaric acid.

In a preferred embodiment, the process of the present invention comprises the step of coupling Arg-Trp-Pro-Trp-Trp-Pro-Trp-Arg-Arg-Lys-NH$_2$ (SEQ ID NO 2) or a derivative thereof with Ile-Leu wherein the amino group of Ile is protected by an amino protective group.

It is furthermore preferred that the process of the present invention comprise the step of coupling Trp-Trp-Pro-Trp-Arg-Arg-Lys-NH$_2$ (SEQ ID NO 3) or a derivative thereof with Arg-Trp-Pro wherein the amino group of Arg is protected by a protective group Preferably, the process comprises the step of coupling Trp-Arg-Arg-Lys-NH$_2$ (SEQ ID NO 4) or a derivative thereof with Trp-Trp-Pro wherein the amino group of the N-terminal Trp is protected by a protective group The invention is moreover directed, according to a second aspect, to a process for the manufacture of H-Arg-Lys(Boc)-NH$_2$, comprising the steps
(a) coupling Z-Arg-OH.Cl and H-Lys(Boc)-NH$_2$; and
(b) hydrogenolysing Z-Arg-Lys(Boc)-NH$_2$ obtained in step
   (a) preferably in the presence of a Pd catalyst;

The term "Lys(Boc)" is intended to denote a Lysine which amino group side chain is protected by a Boc group.

In a third aspect, the invention is directed to the novel intermediate Z-Arg-Trp-Pro-Trp-Trp-Pro-Trp-Arg-Arg-Lys (Boc)-NH$_2$ (SEQ ID NO 2).

In a fourth aspect, the invention is directed to the novel intermediate Z-Arg-Trp-Pro-OH.

In a fifth aspect, the invention is directed to a process for the manufacture of Z-Arg-Trp-Pro-OH, comprising the step of coupling H-Trp-Pro-OH and Z-Arg-OH.HCl.

In a sixth aspect, the invention is directed to the novel intermediate Z-Trp-Trp-Pro-OH.

In a seventh aspect, the invention is directed to a process for the manufacture of Z-Trp-Trp-Pro-OH, comprising the step of coupling H-Trp-Pro-OH and Z-Trp-OSu.

In an eight aspect, the invention is directed to a process for the manufacture of the intermediate Boc-Ile-Leu-OH, comprising the step of coupling Boc-Ile-NCA with H-Leu-OH.

In a ninth aspect, the invention is directed to the novel intermediate Z-Trp-Arg-Arg-Lys(Boc)-NH$_2$ (SEQ ID NO 4).

In a tenth aspect, the invention is directed to the novel intermediate Z-Trp-Trp-Pro-Trp-Arg-Arg-Lys(Boc)-NH$_2$ (SEQ ID NO 3).

In the processes of the present invention, protective groups are used in general for one or more amino groups in the amino acids or peptide intermediates involved. The use of protective groups is not particularly limited.

By way of illustration, the following protective groups may be employed in the compounds of the invention:
acyl-type protective groups, in particular formyl, trifluoroacetyl, phthaloyl, 4-toluenesulphonyl, benzenesulphonyl and 2-nitrophenylsulphenyl, aromatic urethane-type protective groups such as especially, substituted or unsubstituted benzyloxycarbonyl, p-bromobenzyloxycarbonyl, p-methoxybenzyloxycarbonyl, benzhydryloxycarbonyl, 2-(4-biphenylyl) propyl(2)oxycarbonyl, 2-(3,5-dimethyloxphenyl), propyl(2)oxycarbonyl, and triphenylphosphonoethyloxycarbonyl,
aliphatic urethane-type protective groups, in particular tert-butyloxycarbonyl, diisopropylmethoxycarbonyl, isopropyloxycarbonyl, ethoxycarbonyl, allyloxycarbonyl, 9-fluorenylmethyloxycarbonyl, 2-methylsulphonylethyloxycarbonyl and 2,2,3-trichloroethyloxycarbonyl, cycloalkyl urethane-type protective groups such as especially cyclopentyloxycarbonyl, adamantyloxycarbonyl, cyclohexyloxycarbonyl, tert-amyloxycarbonyl and isobornyloxycarbonyl,
thiourethane-type protective groups, in particular phenylthiocarbonyl, alkyl-type protective groups such as especially triphenylmethyl (trityl) and benzyl, trialkylsilane groups such as trialkylsilane. Aforementioned protective groups are particularly suitable as amino protective groups.

It is preferred, in the process(es) of the present invention, that at least one amino group in an amino acid group is protected during a coupling step with a protective group selected from an aromatic urethane-type protective groups and aliphatic urethane-type protective groups. More preferably, said protective group is selected from a t-butyloxycarbonyl (Boc) group and a benzyloxycarbonyl (Z) group.

In a preferred embodiment of the process(es) of the present invention, the benzyloxycarbonyl (Z) group is used as a protective group for a terminal amino group in an amino acid unit, wherein the amino acid unit is either Arg or Trp.

In another preferred embodiment of the process(es) of the present invention, the t-butyloxycarbonyl (Boc) group is used as a protective group for the side chain amino group in Lys and/or the N-terminal amino group in Ile.

Other protective groups, suitable in particular for protection of the carboxyl group include alkoxy groups, in particular methyl ester, ethyl ester, tert-butyl ester and benzyl ester. In a preferred embodiment, the carboxyl group of Lys is protected as amide, in particular as CONH$_2$ group.

In the process(es) of the present invention, the first peptide has an activated carboxy group and generally at least two amino acid units. Various activating groups may be used in the process of the invention that reduce side reactions and/or increase reaction efficiency, preferably chosen from carbodiimides, carbonyldiimidazoles, acyl halides, phosphonium salts and uronium or guanidinium salts. For example, phosphonium and uronium salts can, in the presence of a tertiary base, for example, diisopropylethylamine (DIPEA) and triethylamine (TEA), convert protected amino acids into activated species (for example, BOP, PyBOP, HBTU, and TBTU all generate HOBt esters). Other reagents which help prevent racemization include carbodiimides (for example, N,N-dicyclohexylcarbodiimide (DCC), N-(3-dimethylaminopropyl)-N'-ethylcarbodiimide (EDC) or water soluble carbodiimide (WSCDI)) with an added auxiliary nucleophile (for example, 1-hydroxy-benzotriazole (HOBt), 3,4-dihydro-3-hydroxy-4-oxo-1,2,3-benzotriazine (HOOBT), 1-hydroxy-azabenzotriazole (HOAt), or HOSu) or derivatives thereof. Another reagent that can be utilized is TBTU. Good results were for example obtained with N,N-dicyclohexylcarbodiimide (DCC), N-(3-dimethylaminopropyl)-N'-ethylcarbodiimide (EDC), pivaloyl chloride (PivCl), i-butylchloroformate (IBCF), HBTU (O-(Benzotriazol-1-yl)-N,N,N',N'-tetramethyl uronium hexafluorophosphate), HATU (O-(7-Azabenzotriazol-1-yl)-N,N,N',N'-tetramethylammonium uronium hexafluorophosphate), and EEDQ (2-ethoxy-1-ethoxycarbonyl-1,2-dihydroquinoline).

Preferred activating groups according to the present invention are DCC, EDC and HBTU.

When such carboxylic acid activating agents are used, the coupling reaction is often carried out in the presence of a base as additional reagent. In another particular aspect of the present invention, the coupling reaction is thus carried out in the presence of a base. The base is preferably chosen from tertiary and heteroaromatic amines such as N-methylmorpholine (NMM), pyridine, triethylamine (TEA), diisopropylethylamine (DIPEA) or mixtures thereof. More preferably, it is chosen from N-methylmorpholine and diisopropylethylamine.

In addition to these activating groups, additives are sometimes used advantageously. Preferred additives are N-hydroxysuccinimide (Suc-OH), N-hydroxybenzotriazole (HOBt), or 3,4-dihydro-3-hydroxy-4-oxo-1,2,3 benzotriazine (HOOBt) and derivatives thereof. These additives are usually used in an amount of 1 to 2 equivalents, based upon the amount of carboxyl group to be activated.

In another particular aspect of the present invention, the peptide coupling as above described is carried out in the presence of at least one polar organic solvent. In a particular preferred embodiment, the polar organic solvent allows for particularly efficient control of racemization of the peptide bond formed, the solubility of the peptide and/or peptide fragments, and the coupling reaction rate. The polar organic solvent is preferably selected from N,N-dimethylacetamide (DMA), N,N-dimethylformamide (DMF), N-methylpyrrolidone (NMP), dimethylsulfoxide (DMSO), ethyl acetate (AcOEt), isopropylacetate, dichloromethane (DCM), methylene chloride, pyridine, chloroform, acetonitrile, dimethoxyethane, dioxane, tetrahydrofuran (THF) or mixtures thereof. More preferably, it is selected from N,N-dimethylacetamide (DMA), N-methylpyrrolidone (NMP), dichloromethane (DCM) and N, N-dimethylformamide (DMF) or mixtures thereof. The most preferably, the polar organic solvent is N,N-dimethylacetamide (DMA). A preferred mixture contains 20 to 80% (volume) DMA and 80 to 20% (volume) dichloromethane ($CH_2Cl_2$), more preferably 50 to 70% (volume) DMA and 50 to 30% (volume) dichloromethane ($CH_2Cl_2$).

The terms "coupling" or "coupling step" as used herein refers in particular to the step of coupling different peptides or amino acids.

In a preferred embodiment, the process of the present invention comprises the step of coupling Arg-Trp-Pro-Trp-Trp-Pro-Trp-Arg-Arg-Lys-$NH_2$ (SEQ ID NO 2) or a derivative thereof with protected Ile-Leu or a derivative thereof. In this step, HOOBt is preferably used as an additive. Moreover, this coupling step is preferably carried out in a mixture of DMA/dichloromethane ($CH_2Cl_2$) that preferably contains 50 to 75% (volume) DMA and 25 to 50% (volume) dichloromethane ($CH_2Cl_2$). The coupling step is moreover preferably carried out in the presence of EDC.

In a particularly preferred embodiment of the process according to the invention the second peptide has a formula selected from $NH_2$-Trp-Arg-Arg-Lys(X)-R (SEQ ID NO 4) $NH_2$-Pro-Trp-Arg-Arg-Lys(X)-R (SEQ ID NO 5), $NH_2$-Trp-Pro-Trp-Arg-Arg-Lys(X)-R (SEQ ID NO 6), $NH_2$-Trp-Trp-Pro-Trp-Arg-Arg-Lys(X)-R (SEQ ID NO 7), $NH_2$-Pro-Trp-Trp-Pro-Trp-Arg-Arg-Lys(X)-R (SEQ ID NO 8), $NH_2$-Trp-Pro-Trp-Trp-Pro-Trp-Arg-Arg-Lys(X)-R (SEQ ID NO 9), $NH_2$-Arg-Trp-Pro-Trp-Trp-Pro-Trp-Arg-Arg-Lys(X)-R (SEQ ID NO 10), $NH_2$-Leu-Arg-Trp-Pro-Trp-Trp-Pro-Trp-Arg-Arg-Lys(X)-R (SEQ ID NO 11), where X is a protective group for the Lys-side-chain amino group, preferably a Boc group, and R is a carboxyl protective group for the carboxyl group of Lys, preferably an amide group.

The present invention allows in fact controlling and minimizing throughout the synthesis the presence of products containing the D-enantiomer of Arg in the 10 position of the Ominagan peptide.

In this embodiment, the second peptide generally comprises from 0.1-1 wt %, advantageously from 0.2-0.9 wt % and often from 0.2-0.7 wt % of the peptide selected from $NH_2$-Trp-(D)Arg-Arg-Lys(X)-R (SEQ ID NO 4), $NH_2$-Pro-Trp-(D)Arg-Arg-Lys(X)-R (SEQ ID NO 5), $NH_2$-Trp-Pro-Trp-(D)Arg-Arg-Lys(X)-R (SEQ ID NO 6), $NH_2$-Trp-Trp-Pro-Trp-(D)Arg-Arg-Lys(X)-R (SEQ ID NO 7), $NH_2$-Pro-Trp-Trp-Pro-Trp-(D)Arg-Arg-Lys(X)-R (SEQ ID NO 8), $NH_2$-Trp-Pro-Trp-Trp-Pro-Trp-(D)Arg-Arg-Lys(X)-R (SEQ ID NO 9), $NH_2$-Arg-Trp-Pro-Trp-Trp-Pro-Trp-(D)Arg-Arg-Lys(X)-R (SEQ ID NO 10), $NH_2$-Leu-Arg-Trp-Pro-Trp-Trp-Pro-Trp-(D)Arg-Arg-Lys(X)-R (SEQ ID NO 11) and $NH_2$-(D)Leu-Arg-Trp-Pro-Trp-Trp-Pro-Trp-Arg-Arg-Lys(X)-R (SEQ ID NO 11) wherein X and R are as above described. The invention concerns also said second peptides.

In a further preferred embodiment, the second peptide is $NH_2$-Arg-Lys(X)-R wherein X is an optional protective group for the Lys-side-chain amino group, preferably a Boc group, and R is a carboxyl protective group for the carboxyl group of Lys, preferably an amide group and the first peptide is selected from the group Y-Trp-Arg, Y-Pro-Trp-Arg, Y-Trp-Pro-Trp-Arg (SEQ ID NO 12), Y-Trp-Trp-Pro-Trp-Arg (SEQ ID NO 13), Y-Pro-Trp-Trp-Pro-Trp-Arg (SEQ ID NO 14), Y-Trp-Pro-Trp-Trp-Pro-Trp-Arg (SEQ ID NO 15), Y-Arg-Trp-Pro-Trp-Trp-Pro-Trp-Arg (SEQ ID NO 16), Y-Leu-Arg-Trp-Pro-Trp-Trp-Pro-Trp-Arg (SEQ ID NO 17), Y-Ile-Leu-Arg-Trp-Pro-Trp-Trp-Pro-Trp-Arg (SEQ ID NO 18) and Y is an amino protective group for the N-terminal amino group, in particular as defined above, preferably a Z group.

In this particular embodiment the coupling is advantageously carried out in the presence of an aryl annulated oxotriazine activator, preferably HOOBt.

In this embodiment, the coupling is generally carried out at a temperature from −10 to +10° C.

In this embodiment, the coupling is often carried out in a mixture of a halogenated and a non-halogenated solvent, preferably a mixture of a chlorinated solvent and an amide type solvent. Suitable chlorinated solvents include, for example, chloroform, 1,2-dichloroethane and preferably, dichloromethane. Suitable amide type solvents include, for example, N-methylpyrollidone, N,N-dimethylformamide and, preferably N,N-dimethylacetamide. A mixture of methylene chloride with N,N-dimethylacetamide has given good results.

It is particularly advantageous to couple Z-Trp-Arg-OH with HCl.H-Arg-Lys(Boc)-$NH_2$.

In a most preferred aspect of this embodiment Z-Trp-Arg-OH is coupled with HCl.H-Arg-Lys(Boc)-$NH_2$, the activator is HOOBt, the solvent is a mixture of DMA and methylene chloride and the coupling is carried out in a first time period at a temperature of −5±5° C. for a time from 3 to 5 hours and in a second time period at a temperature of +5±5° C. for a time from 6 to 10 hours.

Particularly preferred processes according to the invention are according to the scheme of FIG. 1. X and Y in the scheme may be the same or different. They are preferably different. Good results were obtained when X was a t-butyloxycarbonyl (Boc) group and Y was a benzyloxycarbonyl (Z) group.

The invention concerns also a deprotection process for the manufacture of the peptide Omiganan with the sequence H-Ile-Leu-Arg-Trp-Pro-Trp-Trp-Pro-Trp-Arg-Arg-Lys-$NH_2$ (SEQ ID NO 1) which comprises reacting a precursor peptide of formula Y1-Ile-Leu-Arg-Trp-Pro-Trp-Trp-Pro-Trp-Arg-Arg-Lys(Y2)-NH$_2$ (SEQ ID NO 1) wherein Y1 and Y2 designate identical or different amino protective groups or H, and at least one of Y1 or Y2 is an acid labile amino protective group, with an acid under substantially anhydrous conditions.

Protective groups Y1 and Y2 can be for example, amino protective groups included in the general description above. It is preferable that both Y1 and Y2 are amino protective groups. More preferably both Y1 and Y2 are Boc.

In the deprotection process according to the invention, the acid is often selected from HCl, HF, HBr, HI, trifluoroacetic acid and trifluoromethanesulphonic acid. More preferably the acid is HCl. In particular in this case preferably 6 to 32 moles, more preferably 12 to 24 moles of acid are used per mole of peptide.

The reaction of the deprotection process according to the invention is generally carried out in an organic solvent, preferably in an aliphatic, in particular a secondary, alcohol, more preferably in isopropanol.

In the deprotection process according to the invention, substantially anhydrous conditions are accomplished, for example, by carrying out the reaction in a liquid reaction medium containing from 10 mg/kg to 1.5 wt %, preferably 50 mg/kg to 1 wt % of water. More preferably the water content of the reaction medium is from 100 mg/kg to 0.5 wt %.

Especially when at least one of Y1 and Y2 is Boc, the reaction is advantageously carried out in the presence of a scavenger for carbocations, in particular the tert.butyl cation, for example, thioanisol and, preferably, 4-(methylthio)phenol.

The reaction of the deprotection process according to the invention is generally carried out at a temperature of from 0° C. to 80° C., preferably from 25° C. to 45° C.

In the deprotection process according to the invention, the peptide Omiganan is advantageously recovered in the form of its pentahydrochloride salt.

In the deprotection process according to the invention, the precursor peptide is preferably obtained by the process according to the invention.

In a particularly preferred embodiment of the deprotection process, deprotection of Boc-Ile-Leu-Arg-Trp-Pro-Trp-Trp-Pro-Trp-Arg-Arg-Lys(Boc)-NH$_2$ (SEQ ID NO 1) to yield 5HCl.H-Ile-Leu-Arg-Trp-Pro-Trp-Trp-Pro-Trp-Arg-Arg-Lys-NH$_2$ (SEQ ID NO 1) is carried out in a mixture of HCl and a secondary alcohol, preferably in the presence of a scavenger for tert-butyl carbocations, for example, 4-(methylthio)phenol. Most preferably, a mixture of HCl and isopropanol is used. The deprotected product obtained in this way can be purified in a particularly economic and efficient manner and more efficient than with other possible deprotection methods including inter alia cleavage with acetic acid, trifluoroacetic acid, methane sulfonic acid, HF and HBr. The Applicant has found, for example, that an HCl/isopropanol mixture, preferably in the presence of a scavenger for tert-butyl carbocations gave better results, rather than a procedure carried out with trifluoroacetic acid (TFA) which is a source of more side-products for tryptophan rich peptides like Omiganan. Also, in this particular case, deprotection is preferably carried out in a reaction medium substantially free of water as described above. Also, in this particular case, said deprotection reaction is advantageously carried out at a temperature of from 20 to 80° C., preferably of from 25 to 45° C. and more preferably of from 30 to 40° C.

In embodiments of the present invention, a hydrogenolysis is carried out in the presence of a catalyst. Preferably, a Pd catalyst is used that can be employed in combination with various supports, for example carbon, SiO$_2$, Si—Al-compounds etc.

In one particular embodiment, the process according to the invention comprises forming a tetraphenylborate salt of an Arg containing peptide. Typically said tetraphenylborate salt of an Arg containing peptide is formed by contacting a coupling step reaction medium containing an Arg containing peptide, which is usually obtained by a coupling step according to the process according to the invention with a source of tetraphenylborate anions. Tetraphenylborate salts are suitable as source of tetraphenylborate anions.

Hence, it is preferred to perform at least one step in the presence of a tetraphenylborate salt (TPB) which is preferably added after the completion of at least one coupling step.

The cation in the tetraphenylborate (TPB) salt can be inorganic or organic. Examples of organic ions are the tetraethylammonium, diisopropylethylammonium, N-ethylpiperidinium, N-methylmorpholinium, N-ethylmorpholinium. Suitable inorganic ions are for example the sodium (Na$^+$) or lithium (Li$^+$). Most preferably, a tetraphenylborate salt is used that is capable of forming an aqueous solution. Preferred are LiTPB and NaTPB. The most preferably used tetraphenylborate salt is NaTPB.

The TPB anion can be substituted on its benzene ring or it can be used without any substitution. Preferably, the TPB anion is not substituted. Examples of suitable substituted TPB anions include, for example, the tetrakis(3,5-bistrifluoromethylphenyl)borate.

The quantity of the tetraphenylborate salt employed may vary within wide limits. Preferably, from 1 to 10 equivalents, preferably 1 to 1.5 equivalents of tetraphenylborate salt is employed per Arg unit in the Arg containing peptide.

The tetraphenylborate salt is preferably employed in the process of the present invention during the work-up after the completion of at least one coupling step, in the presence of a solvent or a mixture of solvents. Suitable solvents are especially methanol, methoxyethanol, dichloromethane, n-butanol, iso-butanol, sec-butanol, and tert-butanol. Good results were obtained using methoxyethanol.

In this embodiment, said tetraphenylborate salt of an Arg containing peptide can advantageously be subjected without isolation to at least one further synthesis step. Often, said tetraphenylborate salt of an Arg containing peptide is subjected at least to a deprotection step followed by a coupling step.

In a most preferred embodiment, the present invention is directed to a process for the manufacture of the peptide Omiganan comprising the following steps (a) to (d):

(a) Coupling of Arg-Lys-NH$_2$ or a derivative thereof, in particular of Arg-Lys(Boc)-NH$_2$, with N-protected Trp-Arg-OH or a derivative thereof, in particular with Z-Trp-Arg-OH.

(b) Coupling of Trp-Arg-Arg-Lys-NH$_2$ (SEQ ID NO 4) or a derivative thereof, in particular of Trp-Arg-Arg-Lys(Boc)-NH$_2$ (SEQ ID NO 4), with N-protected Trp-Trp-Pro or a derivative thereof, in particular with Z-Trp-Trp-Pro-OH.

(c) Coupling of Trp-Trp-Pro-Trp-Arg-Arg-Lys-NH$_2$ (SEQ ID NO 3) or a derivative thereof, in particular of Trp-Trp-Pro-Trp-Arg-Arg-Lys(Boc)-NH$_2$ (SEQ ID NO 3), with N-protected Arg-Trp-Pro or a derivative thereof, in particular with Z-Arg-Trp-Pro-OH.

(d) Coupling of Arg-Trp-Pro-Trp-Trp-Pro-Trp-Arg-Arg-Lys-NH$_2$ (SEQ ID NO 2) or a derivative thereof, in particular Arg-Trp-Pro-Trp-Trp-Pro-Trp-Arg-Arg-Lys(Boc)-NH$_2$ (SEQ ID NO 2), with N-protected Ile-Leu or a derivative thereof, in particular with Boc-Ile-Leu-OH.

The most preferred embodiment of the process comprising steps (a), (b), (c) and (d) is illustrated by the scheme of FIG. 1.

The operating conditions employed in the processes according to the present invention are in general not critical for the invention. Thus, the pressure at which the process is performed is generally so as to maintain the reaction medium in a liquid state, advantageously between 0,1 and 10 bars. Good results have been obtained at atmospheric pressure. The temperature at which the process is performed is usually between −50° and 100° C. and may vary depending on the nature of the reactants in a particular step and the compound which it is ultimately intended to prepare. Preferably, the temperature is greater than or equal to −45° C., more preferably it is greater than or equal to −25° C. On the other hand, the temperature is preferably lower than or equal to 60° C., more preferably it is greater than or equal to 50° C.

In specific coupling steps, preferred, more restricted temperature ranges may apply. For example in the step of coupling Arg-Trp-Pro-Trp-Trp-Pro-Trp-Arg-Arg-Lys-$NH_2$ (SEQ ID NO 2) or a derivative thereof with protected Ile-Leu or a derivative thereof, it is preferred to carry out the coupling reaction in a first time period in a temperature range of 0° C.±5° C., preferably for about 3 to 5 hours, and in a second time period in a temperature range of 20° C.±5° C., preferably for about 6 to 10 hours.

In a preferred embodiment of the process of the invention, the intermediate Z-Trp-Arg-Arg-Lys(Boc)-$NH_2$.2TPB (SEQ ID NO 4) is utilized. Preferably, Z-Trp-Arg-Arg-Lys(Boc)-$NH_2$.2TPB (SEQ ID NO 4) is obtained by coupling Z-Trp-Arg-OH and HCl.H-Arg-Lys(Boc)-$NH_2$. Preferably, this coupling step is carried out in the presence of HOOBt.

In this coupling step, the temperature is preferably maintained in a first time period in a range of from to −5±5° C. for about 2 to 5 hours, and in a second time period in a temperature range of 5±5° C. for about 6 to 10 hours.

The coupling of Z-Trp-Arg-OH and HCl.H-Arg-Lys(Boc)-$NH_2$ is preferably followed by a step (to be called also a work-up step) comprising the addition to the reaction medium of the coupling step of a NaTPB salt, preferably in aqueous solution, more preferably in the presence of $Na_2CO_3$.

In the coupling step(s) of the present invention, one peptide is preferably used in an amount of 0.8 to 1.2 moles of peptide per mole of the other peptide, more preferably 0.9 to 1.1 and most preferably 0.95 to 1.05 moles of peptide per mole of the other peptide.

For example, the first peptide having an activated carboxy group and generally at least two amino acid units is preferably coupled with the second peptide having a free amino group and at least two amino acid units using an amount of 0.8 to 1.2, more preferably 0.9 to 1.1 moles of the first peptide per mole of the second peptide.

The process of the first aspect of the present invention has numerous advantages:
  It is a very convergent pathway with less reaction steps. In embodiments, where use is made of tetraphenylborate (TPB) salts, it is possible, after a selective extraction with TPB salts, either to precipitate those salts or to proceed with the synthesis without isolation. This provides for an increased flexibility during synthesis. It is not necessary to work with protected Arg on the side chains.
  No protection is needed during synthesis on the indole ring of the tryptophan units. Tryptophan is known to be very sensitive towards strong acidic media (alkylation of the indole nucleus, formation of colored side-products). This is a significant advantage, given the fact that the protection is expensive and later on difficult to eliminate. Hence, in a particular preferred embodiment, in the processes and fragments disclosed herein before, at least one tryptophane unit and preferably all tryptophane units are unprotected.

The process of the present invention also allows to reduce amount of racemisation on Arg 10 and Leu 2 which allows an easier final purification.

Finally, the process of the present invention allows rather smooth conditions for the final deprotection, in particular, if appropriate, the elimination of Boc groups.

the process of the present invention allows moreover, in particular in certain preferred embodiments wherein a first peptide having a C-terminal Pro is used, to further reduce risk of racemisation, allowing for an easier final purification.

In particular, the process of the first aspect of the present invention allows to obtain Omiganan with a significantly reduced amount of the three main side products, namely of H-Ile-Leu-Arg-Trp-Pro-Trp-Trp-Pro-Trp-(D)Arg-Arg-Lys-$NH_2$ (SEQ ID NO 1), H-Ile-(D)Leu-Arg-Trp-Pro-Trp-Trp-Pro-Trp-Arg-Arg-Lys-$NH_2$ (SEQ ID NO 1) through a better control of the racemization during the coupling steps, and of H-Ile-Leu-Arg-Trp-Pro-Trp-Trp-Pro-Trp-Arg-Arg-Lys-OH (SEQ ID NO 1) by avoiding working in a strong acidic aqueous medium.

The Omiganan produced in accordance with the process of the present invention is in general purified in a further purification step, in particular a single purification step.

The invention concerns also a process for the purification of the peptide Omiganan, which comprises subjecting an impure peptide Omiganan to a liquid chromatography, in particular HPLC chromatography, with a mobile phase comprising water and an organic solvent. Among HPLC chromatography techniques, reversed phase and ion exchange phase chromatography are preferred. Excellent results were obtained using reversed phases. Various reversed phases columns may be used, in particular $C_4$, $C_8$, $C_{18}$ silica-based reversed phases columns.

In this process, the mobile phase comprises preferably acetonitrile. In this process, the mobile phase comprises advantageously a buffer. Good results were obtained using an acetate buffer. A system comprising acetonitrile and an acetate buffer pH 5 is particularly preferred as mobile phase.

The purification process according to the invention often further comprises a counter-ion exchange step. For example, the purified peptide can be washed, preferably on a chromatography column, with a mixture of a chloride salt aqueous solution, in particular an NaCl aqueous solution with an organic solvent, in particular acetonitrile. If appropriate, the purified peptide after ion exchange can be eluted and from the column by a mixture of acetonitrile with water whereby a concentrated solution of purified Omiganan can be obtained.

The purification process according to the invention may also comprise a crystallization step.

The purification process according to the invention, can hence further comprise a concentrating step and optionally a lyophilisation step.

EXAMPLES

The following examples describe the process of the present invention, but are not to be construed as limiting the present invention. If nothing else is indicated, the purity of the compound was more than 98% by weight and the ratios indicated refer to volume ratios.

1. Synthesis of Z-Arg-Lys(Boc)NH$_2$.TPB 1.02 equivalents of Z-Arg-OH.HCl (Mw=−344.8) were added at room temperature to a mixture of DMA and CH$_2$Cl$_2$ (6/4). Thereafter, 1.03 equivalents of HOBt (N-Hydroxybenzotriazole, Mw=135.12) and 1.00 equivalent of H-Lys(Boc)-NH$_2$ (Mw=245.2; purity: 99%) were added. After cooling the solution to 0±5° C., 1.03 equivalents of EDC.HCl (Mw 191.7) were added.

Stirring was continued for further 30 min at 0±5° C. and then for at least 2 hours at room temperature. After checking for the completion of the reaction by HPLC, the reaction mixture was diluted with a CH$_2$Cl$_2$/iso-BuOH (6/4) mixture and extracted with a solution of 0.5 eq. of HCl. The acidic aqueous phase was extracted a second time with a mixture of CH$_2$Cl$_2$/iso-BuOH (6/4). The combined organic phases were first washed with a 5% (weight) aqueous solution of Na$_2$CO$_3$ containing 1.05 equivalents of sodium tetraphenylborate (TPBNa) (Mw=342 g,), and then 4 times with a 5% (weight) aqueous NaCl solution.

After the organic phase had been concentrated in vacuo, methoxyethanol was added in several portions to the concentrate to eliminate traces of iso-butanol. It was then further evaporated. The concentrate was then finally diluted with methoxyethanol and slowly added to a cold (0 to 5° C.) 5% (weight) aqueous NaCl solution. The peptide precipitated and was kept for at least 30 min at low temperature and then filtered.

The solid was washed 3 times with cold (0±5° C.) demineralised water. Thereafter, the solid was redissolved in MeOH and stirred until a slightly cloudy solution was obtained. The solution was partially concentrated and the methanolic solution was then added slowly to a cooled aqueous NaCl 5% (weight) solution. The precipitate was kept for at least 30 min at low temperature before it was filtered off. Finally the solid was washed 3 times with cold demineralised water (0° C.±5° C.) and dried under vacuum (45° C.). An off white solid was finally obtained. The yield based on the NMR measurement of the content was 89%.

2. Synthesis of HCl.H-Arg-Lys(Boc)-NH$_2$

A methanol solution of 1.00 equivalent of TPB.Z-Arg-Lys(Boc)-NH$_2$ (Mw=535.6; purity=62.0%) was passed several times through a column containing a methanol washed resin IRA 958 (Mw=1000; 3.00 equivalents). After checking the exchange by HPLC, the resin was filtered and washed three times with methanol. The combined organic phases were partially concentrated in vacuo. The concentrated solution was diluted with water.

Pd catalyst (Mw=106.4; 2% weight) were added and the suspension then hydrogenated for at least 5 hours at 35±5° C. The catalyst was filtered off, washed twice with a mixture methanol/water. The filtrate was evaporated in vacuo, the residue suspended in DMA and partially evaporated in vacuo in order to eliminate traces of water. After checking the water content, the final solution was titrated by HCl (0.1N) and further used without any purification.

Yield (based on the titration): 90%.

3. Synthesis of Z-Trp-Arg-OH 2.00 equivalents water and 1 equivalent Arg (Mw=174.2) were mixed with DMF and stirred at room temperature until a solution was obtained. 1.03 equivalents of Z-Trp-OSu (Mw=435.45; purity=98%) were dissolved in DMF and poured in the arginine solution. Stirring was then continued at room temperature for at least 5 hours. After checking the termination of the reaction by HPLC, the reaction mixture was precipitated by adding slowly cold acetonitrile (0±5° C.) and kept at this temperature for at least 30 minutes before filtration. The precipitate was washed 3 times with a mixture of CH$_3$CN/IPE(Isopropylether) (1/1) and then 2 times with IPE. The solid was then dried in vacuo at 45° C. A white solid was finally obtained.

Yield (based on NMR content): 86%.

4. Synthesis of Z-Trp-Arg-Arg-Lys(Boc)-NH$_2$.2TPB (SEQ ID NO 4)

1.00 equivalent Z-Trp-Arg-OH (Mw=494.5; purity=85.0%,) and 1.10 equivalents HOOBt (Mw=163.13) were added to the DMA solution of 1.15 equivalents HCl.H-Arg-Lys(Boc)-NH$_2$ (Mw=437.5; purity=20.0%;) which had been previously diluted with CH$_2$Cl$_2$. After cooling the solution to −5±5° C., 1.00 equivalent HCl/dioxane 4N was slowly poured in and then 1.10 equivalents EDC (Mw=191.7) were added. The reaction mixture was stirred at −5±5° C. for at least 3 hours and then at least for 8 hours at 5±5° C. After checking the completion of the reaction by HPLC, the reaction mixture was diluted with a CH$_2$Cl$_2$/sec-butanol mixture (6/4), washed first with a 5% (weight) aqueous solution of NaCl containing HCl (0.5 eq.), then with 1900 ml of a 5% (weight) aqueous solution of Na$_2$CO$_3$ containing 2.2 equivalents NaTPB (Mw=342), and finally five times with a 5% (weight) aqueous solution of NaCl. After the concentration of the organic layer, the residue was dissolved in methanol and then concentrated in vacuo in order to eliminate most of the remaining CH$_2$Cl$_2$. This final solution was titrated by NMR and further used without any purification.

Yield (based on titration content)=83%.

5. Synthesis of 2HCl.H-Trp-Arg-Arg-Lys(Boc)-NH$_2$ (SEQ ID NO 4)

The methanol solution of 1.00 equivalent of 2TPB.Z-Trp-Arg-Arg-Lys(Boc)-NH$_2$ (Mw=878.11) were passed several times through a column containing 6.00 equivalents of a methanol washed resin IRA 958 (Mw=1000). After checking the exchange by HPLC, the resin was filtered and washed three times with methanol. The combined organic phases were partially concentrated in vacuo. The concentrated solution was diluted with water and Pd catalyst were added. The suspension was then hydrogenated for at least 3 hours at 35±5° C. The catalyst was filtered off and washed twice with methanol. The filtrate was evaporated in vacuo, the residue dissolved in DMA and further concentrated in order to eliminate the remaining water. After the water content was checked, the precipitate was dissolved in DMA and partially evaporated in vacuo in order to adapt the weight of the solution. The final solution was titrated by 0.1N HCl and further used without any purification.

Yield (based on the titration): 95%.

6. Synthesis of Z-Trp-Trp-Pro-OH

DMA, 1.05 equivalents of DIPEA (Mw=129.2) and 1.05 equivalents of H-Trp-Pro-OH (Mw=301.3; purity=91.0%) were mixed at room temperature for at least 30 min until a solution had formed. The reaction mixture was then diluted with ethyl acetate and cooled to 5±5° C. Once this temperature was reached, 1.00 equivalent of Z-Trp-OSu (Mw=435.45; purity=98.0%) was added and stirring continued for at least 30 min before the solution was left to warm up to room temperature again. After the completion of the reaction was confirmed by HPLC, 0.2 eq of, DMAPA (N,N'-Dimethylaminopropylamine, Mw=102.2 g/mol) were added. The reaction mixture was diluted with ethyl acetate and washed with a 5% (weight) aqueous NaCl solution containing 2 equivalents of KHSO$_4$. The organic phase was further washed first with a 5% (weight) aqueous NaCl solution and finally with water. The organic phase was partially concentrated in vacuo and the residue was suspended in ethyl acetate and further concentrated in order to eliminate the remaining water. The concentrated peptide solution was added in small portions to a cold (0±5° C.) mixture of MTBE/petroleum ether (45-55) (1/1) and the precipitate was kept at 0±5° C. for at least 30 min before filtration. After filtration, it was then washed with petroleum ether (45-55) and dried in vacuo at 45° C. A white solid was finally obtained.

Yield (based on NMR content)=82%

7. Synthesis of Z-Trp-Trp-Pro-Trp-Arg-Arg-Lys(Boc)-NH$_2$.2TPB (SEQ ID NO 3)

1.00 equivalent of Z-Trp-Trp-Pro-OH (Mw=621.7; purity=94.0%) was added to the DMA solution of 1.05 equivalents 2HCl.HTrp-Arg-Arg-Lys(Boc)-NH$_2$ (Mw=816.9; purity=15.0%) previously diluted with CH$_2$Cl$_2$. Then, 1.20 equivalents N,N'-Diisopropylethylamine (DIPEA) (Mw=129.2) and 1.05 equivalents of 2-(1H-benzotriazole-1-yl)-1,1,3,3-tetramethyluroniumhexafluorophosphate) (HBTU) (Mw=379.24) were added. The reaction mixture was stirred at room temperature for at least 1 hour. After checking the completion of the reaction by HPLC, the reaction mixture was diluted with a CH$_2$Cl$_2$/iso-butanol mixture (8/2), washed first with a 5% (weight) aqueous solution of NaCl and HCl (1.5 eq.), then with a 5% (weight) aqueous solution of Na$_2$CO$_3$ and 2.2 equivalents NaTPB (Mw=342 g/mol), and finally three times with a 5% (weight) aqueous solution of NaCl. After concentration of the organic layer, the residual oil was several times dissolved in methoxyethanol, then concentrated in vacuo in order to eliminate most of the remaining iso-butanol. After GC control, the concentrate was precipitated by slowly pouring it into cold (0±5° C.) 5% (weight) aqueous solution of NaCl. After stirring for at least 1 hour, the suspension was filtered and washed twice with cold water. The precipitate was dried in vacuo at 45° C. A white solid was finally obtained.

Yield (based on NMR content)=98%.

8. Synthesis of 2HCl.H-Trp-Trp-Pro-Trp-Arg-Arg-Lys(Boc)-NH$_2$ (SEQ ID NO 3)

A methanol solution of 1.00 equivalent of 2TPB.Z-TrpTrp-Pro-Trp-Arg-Arg-Lys(Boc)-NH$_2$ (Mw=1347.5; purity=64.0%) was passed several times through a column containing a methanol washed resin IRA 958 (or Amberjet Cl 1000; 6.00 equivalents). After checking the exchange by HPLC, the resin was filtered, washed three times. The combined organic phases were partially concentrated in vacuo and then diluted with water. Finally, 2% (weight) of Pd catalyst were added and the suspension hydrogenated for at least 3 hours at 40° C. The catalyst was filtered off, washed three times with a mixture of methanol/water. The combined filtrates were evaporated in vacuo, the residue suspended in DMA and further concentrated in order to eliminate the remaining water. After checking the water content, the solution was titrated by HCl (0.1 N), AgNO$_3$ (0.1 N) or NMR and further used without any purification.

Yield (based on titration)=82%.

9. Synthesis of Z-Arg-Trp-Pro-OH

DMA, 1.00 equivalent of DIPEA and 1.00 equivalent of H-Trp-Pro-OH (Mw=301.3; purity=94.0%) were mixed at room temperature for at least 30 min until a solution was obtained and then the solution was cooled to 10±5° (solution No. 1). 1.00 equivalent of Z-Arg-OH.HCl (Mw=344.8) were added to DMA at room temperature until a clear solution was obtained (solution No. 2). While cooling solution No. 2 to −15±5° C., 1.05 equivalents pyridine (Mw=79.1; purity=99.0%) and 1.00 equivalent of DIPEA were added. Once this temperature was reached, 1.00 equivalent of pivaloyl chloride (PivCl) (Mw=120.58) was poured into the reaction mixture (solution No. 2) which was further activated for about 5 minutes. Finally, solution No. 1 was added to the activated solution No. 2 and the reaction mixture was further stirred for at least 1 hour while cooling was stopped and the reaction mixture allowed to warm up to room temperature.

After the completion of the reaction had been confirmed by HPLC, the peptide solution was concentrated in vacuo. The residue was diluted with acetonitrile and water and the pH was adjusted to 8.0±0.2 by 2N K$_2$CO$_3$. The solution was then partially concentrated in vacuo and the residue was cooled to 5±5° C. to precipitate. Stirring was maintained for at least 30 min before filtration and the precipitate then washed with water. A white solid was finally obtained.

Yield (based on NMR content): 90%.

10. Synthesis of Z-Arg-Trp-Pro-Trp-Trp-Pro-Trp-Arg-Arg-Lys(Boc)-NH$_2$.3TPB (SEQ ID NO 2)

1.00 equivalent of Z-Arg-Trp-Pro-OH (Mw=591.65; purity=96.0%), 1.00 equivalent of HCl/dioxane (4N;) and 1.05 equivalents HOBt (Mw=135.12; purity=98.0%) were added to 1.00 equivalent 2HCl.H-Trp-Trp-Pro-Trp-Arg-Arg-Lys(Boc)-NH$_2$ (Mw=1213.4; purity=85.0%;) in solution in DMA diluted with CH$_2$Cl$_2$. After the solution had been cooled to 10±5° C., 1.02 equivalents EDC (Mw=191.7) were added. The reaction mixture was stirred at 10±5° C. for 30 min and then at least 4 hours at room temperature. After the completion of the reaction was confirmed by HPLC, the reaction mixture was diluted with a CH$_2$Cl$_2$/iso-butanol mixture (8/3), washed first with a 5% (weight) aqueous NaCl solution with HCl (0.5 eq.), then with a 5% (weight) aqueous solution of Na$_2$CO$_3$, containing 3 eq NaTPB (Mw=342), and finally twice with a 5% (weight) aqueous solution of NaCl. After concentration of the organic layer, the residual oil was several times dissolved in methoxyethanol, then concentrated in vacuo in order to eliminate most of the iso-butanol. After GC control, the concentrate was precipitated by slowly pouring it into cold 5% (weight) aqueous solution of NaCl. After stirring for at least 1 hour, the suspension was filtered, washed twice with cold water. The precipitate was dried at 40±5° C. An off white solid was finally obtained.

Yield (based on NMR content)=87%.

11. Synthesis of 3HCl.H-Arg-Trp-Pro-Trp-Trp-Pro-Trp-Arg-Arg-Lys(Boc)-NH$_2$ (SEQ ID NO 2)

A methanol solution of 1.00 equivalent of 3TPB.Z-Arg-Trp-Pro-TrpTrp-Pro-Trp-Arg-Arg-Lys(Boc)-NH$_2$ (Mw=1787.1; purity=57.0%;) was passed several times through a column containing a methanol washed resin IRA 958 (Mw=1000, 9.00 equivalents). After the exchange had been checked by HPLC, the resin was filtered and washed three times with methanol. The combined organic phases were partially concentrated in vacuo. The concentrated solution was then diluted with water and Pd catalyst was added. The suspension was then hydrogenated for at least 6 hours at 35±5° C. The catalyst was filtered off, washed three times with a mixture methanol/water. The combined filtrates were evaporated in vacuo, the residue suspended in DMA and further concentrated in order to eliminate the remaining water. After checking the water content, the solution was titrated by HCl (0.1N) or NMR and further used without any purification.

Yield (based on NMR content measurement): 93%.

12. Synthesis of Boc-Ile-Leu-OH

The synthesis of the dipeptide Boc-Ile-Leu-OH was performed according two pathways:
through the activated ester OSu of Boc-Ile-OH (pathway A)
through the use of the UNCA (Urethane N-protected Carboxyanhydride) of Boc-Ile-OH (pathway B)

Pathway A: Synthesis of Boc-Ile-OSu (Comparative)

Under stirring, 1.00 equivalent of Boc-Ile-OH.1/2 H$_2$O (Mw=240.3) and 1.05 equivalents of Suc-OH (Mw=115) were added to ethyl acetate. The solution was cooled to 0±5° C. and then 1.10 equivalents DCC (Mw=206.3) diluted in ethyl acetate was poured into the solution. The suspension was stirred at 0° C. for at least 30 min and at room temperature for at least 5 hours. After the reaction mixture had been quenched by adding 2.4 g acetic acid (0.20 equivalents), the DCU was filtered and washed twice with ethyl acetate. The organic layers were washed with 5% (weight) aqueous NaCl solution containing 0.5 equivalents $KHSO_4$, 5% (weight) aqueous NaCl solution; 5% (weight) aqueous NaCl solution containing 0.5 equivalents $Na_2CO_3$ and finally with 5% (weight) aqueous NaCl solution. The solvent was concentrated in vacuo. The concentrated solution was twice taken up in ethyl acetate and further evaporated in vacuo in order to eliminate the remaining water. The concentrated organic layer was diluted with cyclohexane or heptane. The precipitated suspension was stirred at room temperature for at least 30 min, filtered and finally dried under vacuum (45° C.). The dried precipitate yielded 89% (based on NMR content) of Boc-Ile-OSu as white solid.

Pathway A: Synthesis of Boc-Ile-Leu-OH 1.01 equivalents of H-Leu-OH (Mw=131.2) was first silylated with 2.10 equivalents TMA (Mw=145.12) at about 50° C. until a clear solution was obtained. The solution was cooled to room temperature and diluted with isopropyl acetate. 1.00 equivalent of the Boc-Ile-OSu solid (Mw=328.26; 100.0%) was then added to silylated H-Leu-OH solution. The reaction mixture was further stirred at room temperature for at least 8 hours. After the completion of the reaction was confirmed by HPLC, the solution was quenched by adding DMAPA and water, washed with $KHSO_4$ (1.00 equivalent) in 500 ml 5% (weight) aqueous NaCl solution; 500 ml 5% (weight) aqueous NaCl solution, and water. After evaporation of the isopropyl acetate in vacuo, the excess of water was eliminated by azeotropic distillation with isopropyl acetate. The peptide precipitated during the concentration. The concentrated suspension was then diluted in cyclohexane. The precipitate was stirred at room temperature for at least 10 min, filtered and finally dried in vacuum at 45° C. The dried precipitate yielded (based on NMR content) 80% of Boc-Ile-Leu-OH as white solid.

Pathway B: Synthesis of Boc-Ile-Leu-OH 1.00 equivalent of Boc-Ile-NCA (Mw=257.3) was added to 1.10 equivalents of H-Leu-OH (Mw=131.2) in suspension in DMSO. The suspension was then heated at 60±5° C. at least 2 hours. After checking the conversion rate by HPLC, the reaction mixture was diluted with isopropyl acetate, washed by $KHSO_4$ (Mw=136; 1.00 equivalent) in NaCl 5% (weight) aqueous, NaCl 5% (weight) aqueous and water. After evaporation of isopropyl acetate in vacuo, the excess of water was eliminated by azeotropic distillation with isopropyl acetate. The peptide precipitated during the concentration. The concentrated suspension was then diluted in cyclohexane. The precipitate was stirred at room temperature for at least 10 min, filtered and finally dried in vacuum at 45° C. The dried precipitate yielded 89% of Boc-Ile-Leu-OH as a white solid (based on NMR content).

13. Synthesis of 3HCl.Boc-Ile-Leu-Arg-Trp-Pro-Trp-Trp-Pro-Trp-Arg-Arg-Lys(Boc)-$NH_2$ (SEQ ID NO 1)

1.05 equivalents of Boc-Ile-Leu-OH (Mw=344.4) and 1.10 equivalents of HOOBt (Mw=163.13) are added to a cold (0±5° C.) solution of 1.00 equivalent of 3HCl.H-Arg-Trp-Pro-Trp-Trp-Pro-Trp-Arg-Arg-Lys(Boc)-$NH_2$ (Mw=1652.9; purity=89.0%) in DMA and $CH_2Cl_2$. 1.20 equivalents of EDC(N-(3-dimethylaminopropyl)-N-ethylcarbodiimide; Mw=191.7; purity=100.0%) was then added to the reaction mixture which was further stirred at 0±5° C. for about 4 hours, then at least 8 hours at room temperature. After the completion of the reaction had been checked by HPLC, the reaction mixture was diluted with a $CH_2Cl_2$/iso-butanol mixture (8/2), and washed with a 5% (weight) aqueous NaCl solution+HCl (0.3 eq.). After concentration of the organic layer, the residual oil was precipitated by slowly pouring into cold (0±5° C.) acetonitrile. After stirring at least for 30 min at 0±5° C., the suspension was filtered and washed twice with cold MTBE. The precipitate was dried at 40±5° C. An off white solid was finally obtained.

Yield (based on NMR content)=88%.

14. Synthesis of 5HCl.H-Ile-Leu-Arg-Trp-Pro-Trp-Trp-Pro-Trp-Arg-Arg-Lys-$NH_2$ (SEQ ID NO 1)

1.00 equivalent of Boc-Ile-Leu-Arg-Trp-Pro-Trp-Trp-Pro-Trp-Arg-Arg-Lys(Boc)-$NH_2$ (SEQ ID NO 1) (Mw=1980; purity=89.0%) was slowly added to isopropanol containing 24 equivalents HCl relative to the peptide and 6 eq. 4-(methylthio)phenol (Mw=124.2). After the addition was completed, the reaction mixture was diluted with isopropanol. The reaction mixture was stirred at least 2 hours at 35±5° C. After checking the completion of the reaction by HPLC, the reaction mixture was slowly poured into cold isopropyl ether. The precipitate was stirred at least 15 min at 0±5° C., then filtered, washed three times with isopropyl ether and finally dried under vacuum to obtain 5HCl.H-Ile-Leu-Arg-Trp-Pro-Trp-Trp-Pro-Trp-Arg-Arg-Lys-$NH_2$ (SEQ ID NO 1).

15. Purification of the 5HCl.H-Ile-Leu-Arg-Trp-Pro-Trp-Trp-Pro-Trp-Arg-Arg-Lys-$NH_2$ (SEQ ID NO 1)

The product obtained in example 14 was dissolved in an acetate buffer and filtered on a 0.5 μm membrane. The resulting solution was purified by a HPLC using the following parameters:

column: 2.0*25 cm (ID*L)
    stationary phase: $C_{18}$ silica; 10 μm-100 A
    mobile phases: A=acetate buffer pH 5.0 (0.15 M)
      B=acetonitrile
    flow: 19 mL/min
    wave length: 254 nm
    gradient (min; B): (0; 10) (5; 10) (6; 18) (36; 33) (36.1; 60) (43; 60) (43.1; 10) (52; 10)

The Omiganan peptide (SEQ ID NO 1) was obtained with a purity of above 98%.

The resulting high purity fractions were diluted with water and the same column was used to change the acetate ions into $Cl^-$ ions using the following mobile phases:

water/acetonitrile 95/5 v/v for the equilibration of the column
    0.5M NaCl/MeCN 95/5 v/v for the ion exchange
    water/MeCN 60/40 v/v for the elution The resulting product was then concentrated and lyophilised.

The invention claimed is:

1. A process for the manufacture of the peptide Omiganan with the sequence H-Ile-Leu-Arg-Trp-Pro-Trp-Trp-Pro-Trp-Arg-Arg-Lys-NH$_2$ (SEQ ID NO: 1) comprising at least one step of coupling, in solution in at least one polar organic solvent, a first peptide having an activated carboxy group, wherein the activating group is chosen from carbodiimides, carbonyldiimidazoles, acyl halides, phosphonium salts and uronium salts, and at least two amino acids, with a second peptide having a free amino group and at least two amino acids wherein the first and second peptides are different and contain amino acids selected from the group consisting of Ile, Leu, Arg, Trp, Pro and Lys in the order as prescribed by the sequence Ile-Leu-Arg-Trp-Pro-Trp-Trp-Pro-Trp-Arg-Arg-Lys (SEQ ID NO: 1) in Omiganan.

2. The process according to claim 1, comprising the step of coupling Arg-Trp-Pro-Trp-Trp-Pro-Trp-Arg-Arg-Lys-NH$_2$ (SEQ ID NO: 2) with Ile-Leu wherein the amino group of Ile is protected by an amino protective group.

3. The process according to claim 1, comprising the step of coupling Trp-Trp-Pro-Trp-Arg-Arg-Lys-NH₂ (SEQ ID NO: 3) with Arg-Trp-Pro wherein the amino group of Arg is protected by a protective group.

4. The process according to claim 1, comprising the step of coupling Trp-Arg-Arg-Lys-NH₂ (SEQ ID NO: 4) with Trp-Trp-Pro wherein the amino group of the N-terminal Trp is protected by a protective group.

5. The process according to claim 1, wherein the second peptide is
NH₂-Arg-Lys(X)-R wherein X is an optional protective group for the Lys-side-chain amino group and R is a carboxyl protective group for the carboxyl group of Lys, and the first peptide is selected from the group consisting of Y-Trp-Arg, Y-Pro-Trp-Arg, Y-Trp-Pro-Trp-Arg (SEQ ID NO: 12), Y-Trp-Trp-Pro-Trp-Arg (SEQ ID NO: 13), Y-Pro-Trp-Trp-Pro-Trp-Arg (SEQ ID NO: 14), Y-Trp-Pro-Trp-Trp-Pro-Trp-Arg (SEQ ID NO: 15), Y-Arg-Trp-Pro-Trp-Trp-Pro-Trp-Arg (SEQ ID NO: 16), Y-Leu-Arg-Trp-Pro-Trp-Trp-Pro-Trp-Arg (SEQ ID NO: 17), and Y-Ile-Leu-Arg-Trp-Pro-Trp-Trp-Pro-Trp-Arg (SEQ ID NO: 18), wherein Y is an amino protective group.

6. The process of claim 1, wherein the coupling is carried out at a temperature from −10° C. to +10° C.

7. The process according to claim 1, wherein the second peptide is represented by a formula selected from the group consisting of NH₂-Trp-Arg-Arg-Lys(X)-R (SEQ ID NO: 4), NH₂-Pro-Trp-Arg-Arg-Lys(X)-R (SEQ ID NO: 5), NH₂-Trp-Pro-Trp-Arg-Arg-Lys(X)-R (SEQ ID NO: 6), NH₂-Trp-Trp-Pro-Trp-Arg-Arg-Lys(X)-R (SEQ ID NO: 7), NH₂-Pro-Trp-Trp-Pro-Trp-Arg-Arg-Lys(X)-R (SEQ ID NO: 8), NH₂-Trp-Pro-Trp-Trp-Pro-Trp-Arg-Arg-Lys(X)-R (SEQ ID NO: 9), NH₂-Arg-Trp-Pro-Trp-Trp-Pro-Trp-Arg-Arg-Lys(X)-R (SEQ ID NO: 10), and NH₂-Leu-Arg-Trp-Pro-Trp-Trp-Pro-Trp-Arg-Arg-Lys(X)-R (SEQ ID NO: 11), wherein X is an optional protective group for the Lys-side-chain amino group, and wherein R is a carboxyl protective group for the carboxyl group of Lys.

8. The process according to claim 7, wherein the second peptide is obtained by a process comprising at least one step of coupling in solution a peptide selected from the group consisting of Y-Trp-Arg, Y-Pro-Trp-Arg, Y-Trp-Pro-Trp-Arg (SEQ ID NO: 12), Y-Trp-Trp-Pro-Trp-Arg (SEQ ID NO: 13), Y-Pro-Trp-Trp-Pro-Trp-Arg (SEQ ID NO: 14), Y-Trp-Pro-Trp-Trp-Pro-Trp-Arg (SEQ ID NO: 15), Y-Arg-Trp-Pro-Trp-Trp-Pro-Trp-Arg (SEQ ID NO: 16), Y-Leu-Arg-Trp-Pro-Trp-Trp-Pro-Trp-Arg (SEQ ID NO: 17), and Y-Ile-Leu-Arg-Trp-Pro-Trp-Trp-Pro-Trp-Arg (SEQ ID NO: 18), wherein Y is an amino protective group, with a peptide: NH₂-Arg-Lys(X)-R wherein X is an optional protective group for the Lys-side-chain amino group and R is a carboxyl protective group for the carboxyl group of Lys.

9. The process according to claim 7, wherein the second peptide comprises from 0.1-1 wt %, of its (D)Arg-Arg-Lys (X)-R analog.

10. The process according to claim 9, wherein the second peptide comprises from 0.2-0.9 wt %, (D)Arg-Arg-Lys(X)-R analog.

11. The process according to claim 1, wherein the coupling is carried out in a mixture of a halogenated and a non-halogenated solvent.

12. The process according to claim 11, wherein the coupling is carried out in the presence of a mixture of N,N-dimethylacetamide and methylene chloride.

13. The process of claim 12, wherein the mixture contains 20 to 80% (volume) N,N-dimethylacetamide and 80 to 20% (volume) methylene chloride.

14. The process of claim 1, wherein the coupling is carried out in the presence of a base.

15. The process of claim 14, wherein the base is selected from the group consisting of N-methylmorpholine, pyridine, triethylamine, diisopropylethylamine and mixtures thereof.

16. The process of claim 1, wherein the coupling is carried out in the presence of an additive selected from the group consisting of N-hydroxysuccinimide, N-hydroxybenzotriazole and 3,4-dihydro-3-hydroxy-4-oxo-1,2,3-benzotriazine.

17. The process of claim 16, wherein the additive is present in an amount of 1 to 2 equivalents, based upon the amount of the activated carboxy group.

18. A process for the manufacture of the peptide Omiganan with the sequence H-Ile-Leu-Arg-Trp-Pro-Trp-Trp-Pro-Trp-Arg-Arg-Lys-NH₂ (SEQ ID NO: 1) comprising at least one step of coupling, in solution in at least one polar organic solvent, a first peptide having an activated carboxy group, wherein the activating group is chosen from carbodiimides, carbonyldiimidazoles, acyl halides, phosphonium salts and uronium salts, and at least two amino acids, with a second peptide having a free amino group and at least two amino acids wherein the first and second peptides are different and contain amino acids selected from the group consisting of Ile, Leu, Arg, Trp, Pro and Lys in the order as prescribed by the sequence Ile-Leu-Arg-Trp-Pro-Trp-Trp-Pro-Trp-Arg-Arg-Lys (SEQ ID NO: 1) in Omiganan, wherein the said second peptide is Arg-Trp-Pro-Trp-Trp-Pro-Trp-Arg-Arg-Lys-NH₂ (SEQ ID NO: 2) or Trp-Trp-Pro-Trp-Arg-Arg-Lys-NH₂ (SEQ ID NO: 3) or Trp-Arg-Arg-Lys-NH₂ (SEQ ID NO: 4).

* * * * *